US00PP27161P2

(12) United States Plant Patent
Kordes

(10) Patent No.: US PP27,161 P2
(45) Date of Patent: Sep. 20, 2016

(54) MINIATURE ROSE PLANT NAMED 'KORPOT063'

(50) Latin Name: *Rosa hybrida*
Varietal Denomination: KORpot063

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes Sohne Rosenschulen Gmbh & Co. KG, Offenseth-Sparrieshoop (DE)

( * ) Notice: Subject to any disclaimer, the term of this patent is extended or adjusted under 35 U.S.C. 154(b) by 100 days.

(21) Appl. No.: 14/544,450

(22) Filed: Jan. 7, 2015

(51) Int. Cl.
*A01H 5/02* (2006.01)

(52) U.S. Cl.
USPC ..... Plt./118

(58) Field of Classification Search
USPC ..... Plt./116, 118
See application file for complete search history.

*Primary Examiner* — Susan McCormick Ewoldt

(57) ABSTRACT

A new and distinct variety of rose with long lasting, novel yellow flowers, and attractive foliage with very good disease resistance. It exhibits compact upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpot063'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 2011. The crossing was between an un-named seedling, the seed parent, and another un-named seedling, the pollen parent by the same inventor.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpot063'.

SUMMARY OF THE INVENTION

The new rose plant may be distinguished from its seed parent, an un-named seedling, by the following combination of characteristics:

1. 'KORpot063' has yellow flowers, whereas the un-named seedling has salmon-orange flowers.
2. 'KORpot063' has large-sized long-lasting flowers, whereas the un-named seedling has small flowers with moderate duration.

The new rose plant may be distinguished from its pollen parent, an un-named seedling, by the following combination of characteristics:

1. 'KORpot063' has yellow flowers, whereas the un-named seedling has cream-colored flowers.
2. 'KORpot063' has a bushy and upright habit, whereas the un-named seedling has a very compact habit.

The objective of the hybridization was to create a new and distinct rose plant with unique qualities, such as:

1. Compact and uniform growth and flowering under greenhouse conditions when grown as a potted floral plant;
2. Abundant, long lasting, and attractive flowers and foliage;
3. Resistance to diseases encountered in greenhouse and nursery culture; and
4. Suitability for production from softwood cuttings in floral and nursery containers.

This combination of qualities is not present in prior rose cultivars known to the inventor. These objectives have been substantially achieved and in that distinguish 'KORpot063' from all other varieties of which I am aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpot063' was selected in April 2012 from the seedling beds to be asexually propagated for further evaluation. The first asexual propagation of 'KORpot063' was done by rooting softwood cuttings in June 2012 at the inventor's nursery in Offenseth-Sparrieshoop, Germany.

These initial and other subsequent propagations conducted in controlled environments demonstrate that 'KORpot063' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot063'.

DETAILED BOTANICAL DESCRIPTION

The following is a description of 'KORpot063', as observed growing in December 2014 in a nursery in Jackson County, Oreg. on plants of 7 months of age. Color references are made using The Royal Horticultural Society (London, England) Colour Chart, 2001 except where common terms of color are used.

For a comparison, several physical characteristics of the rose variety 'KORsmisu', a rose variety from the same inventor described and illustrated in U.S. Plant Pat. No. 21,469 and issued on Nov. 16, 2014 are compared to 'KORpot063' in Chart 1.

CHART 1

| Characteristic | 'KORpot063' | 'KORsmisu' |
|---|---|---|
| General tonality on open flower. | Yellow-Orange Group 16A. | Yellow Group 13B. |
| Number of pistils. | 50 pistils present. | No pistils present. Flowers are incomplete. |
| Open flower diameter. | 65 mm. | 50 mm. |

Parents:

*Seed parent*.—An un-named seedling.

*Pollen parent*.—An un-named seedling.

Classification:

*Botanical classification*.—*Rosa hybrida* 'KORpot063'.

*Commercial classification*.—Miniature rose.

FLOWER AND FLOWER BUD

Blooming habit: Recurrent.

Flower bud:

*Size*.—Upon opening, 25 to 30 mm in length from base of receptacle to distal end of bud and 10 to 15 mm diameter at its widest point.

*Bud form*.—Long. Pointed ovoid.

*Bud color*.—As sepals first unfold, bud color is Yellow Group 1C with intonations of Yellow-Orange Group 16B. When ¼ open, the upper surface of petals is Yellow-Orange Group 17A on the marginal and middle zones, and Yellow Group 9A on the basal zone. The lower surface is Yellow Group 20A on the marginal and middle zones, and Yellow Group 5A on the basal zone.

*Sepals*.—Color: Upper surface: Yellow-Green Group 147B. Lower surface: Yellow-Green Group 146B. Size: Average 35 to 40 mm (l)×6 to 7 mm (w). Diameter of the calyx: 30 to 70 mm. Shape: Very weak foliaceous appendages on three of the five sepals. Apex: Apiculate. Base: Flat at union with receptacle. Quantity: Five. Surface texture: Upper side: Hoary. Lower surface: Glabrous. Margins: Cilliate with a limited number of stipitate glands. Stipitate glands: Limited numbers of stipitate glands present on margins.

Flower bloom:

*Fragrance*.—Light.

*Duration*.—On the plant 15 to 18 days. Senesced petals drop away cleanly.

*Size*.—Large for a miniature rose. When open, the average flower diameter is 65 mm and the average flower height is 40 mm.

*Form*.—Shape: Round. High-centered quartered rosette. Shape of flower when viewed from the side: Upon opening, upper part: Flattened convex. Upon opening, lower part: Flattened convex. Open flower, upper part: Flattened convex. Open flower, lower part: Concave.

Color:

*Upon opening, petals*.—Outermost petals: Outer Side: Yellow-Orange Group 16B on the middle and marginal zones, and Yellow Group 13B on the basal zone. Inner Side: Yellow-Orange Group 15A on the middle and marginal zones, Yellow Group 12A on the basal zone. Innermost petals: Outer Side: Yellow Group 15A on the middle and marginal zones, and Yellow Group 13A on the basal zone. Inner Side: Yellow Group 13A. Basal petal spots: No distinctive coloration at petal base observed.

*After opening, petals*.—Guard Petals: Outer Side: Yellow Group 10A with intonations of Yellow-Green Group 145B, present on circulatory structures. Inner Side: Yellow Group 13A with intonations of Yellow-Green Group 145B, present on the midrib and circulatory structures. Outermost petals: Outer Side: Yellow-Orange Group 20A on the marginal zone, Yellow-Orange Group 16B on the middle zone, and Yellow Group 13A on the basal zone. Inner Side: Yellow-Orange Group 16A on the marginal zone, Yellow-Orange Group 14A on the middle zone, and Yellow Group 13A on the basal zone. Innermost petals: Outer Side: Yellow-Orange Group 16A on the marginal and middle zones, and Yellow Group 13A on the basal zone. Inner Side: Yellow-Orange Group 17B on the marginal and middle zones, and Yellow-Orange Group 14A on the basal zone. Basal petal spots: No distinctive coloration at petal base observed.

General tonality: On open flower Yellow-Orange Group 16A. No change in the general tonality at the end of the 8th day. Afterwards, general tonality is Yellow-Orange Group 16D.

Petals:

*Petal count*.—Very Double. Approximately 45 to 50 petals under normal conditions.

*Petal reflex*.—Strong double reflex observed on outermost petals only. Reflex occurs one by one.

*Petal margin*.—Typically entire, with ruffled edges observed on some innermost petals.

*Petal shape*.—Obovate. Apex: Typically mucronate, with retuse and emarginate apices observed on some innermost petals. Base: Cuneate.

*Petal size*.—20 to 30 mm (l)×10 to 30 mm (w).

*Petal arrangement*.—Formal.

*Texture, outermost petals*.—Inner Side: Rugose. Outer Side: Rugose.

*Texture, innrmost petals*.—Inner Side: Smooth. Outer Side: Smooth.

Petaloids:

*Petaloid count*.—Average of 5 to 10 per flower.

*Petaloid size*.—10 to 15 mm (l)×5 to 10 mm (w).

*Petaloid color*.—Inner side: Yellow-Orange Group 21B with intonations of Red Group 50B and Yellow-Orange Group 18B. Outer side: Yellow-Orange Group 21B with intonations of Red Group 50B and Yellow-Orange Group 18B.

*Petaloid texture*.—Inner Side: Smooth. Outer Side: Smooth.

*Margins*.—Undulated.

*Petaloid shape*.—Most commonly cuneate, with some petaloids highly irregular. Apex: Acute. Base: Attenuate.

Reproductive organs:

*Pistils*.—Average. Approximately 50 present. Stigmas: Location: Slightly superior or equal in position to anthers. Color: Yellow-Group 6D. Diameter: 0.5 to 1 mm. Styles: Length: About 5 to 10 mm long. Color: Yellow Group 2D.

*Stamens*.—Approximately 80 on average and regularly arranged. Anthers: Size: Average 2 to 3 mm (l)×1 to 2 mm (w). Color: Yellow-Orange Group 18B with intonations of Red Group 50B. Pollen: Generally present. Color: Greyed-Orange Group N163C. Filaments: Color: Yellow Group 13A. Length: 5 to 7 mm.

Receptacle:

*Surface*.—Most commonly glaucous.

*Color*.—Yellow-Green Group 146D.

*Shape*.—Urn-shaped.

*Texture*.—Glabrous.

*Size*.—10 mm (h)×8 to 9 mm (w).

Pedicel:

*Surface*.—With limited numbers of stipitate glands.

*Length*.—60 to 70 mm average length.

*Diameter*.—2 to 3 mm average diameter.

*Color*.—Yellow-Green Group 146C, with intonations of Greyed-Red Group 181B.

*Strength*.—Somewhat strong.

*Texture*.—Glabrous to slightly papillate.

*Borne*.—Typically singularly. Multiple flower buds per stem occasionally observed, with 2 to 3 flowers pre inflorescence. Flowering laterals typically absent below initiation of inflorescence. If present, typically 1 to 2 laterals present with 1 to 3 flowers per flower shoot. Flowers pendant.

Peduncle:

*Surface*.—Limited numbers of stipitate glands occasionally present.

*Length*.—30 to 80 mm average length.

*Diameter*.—2 to 3 mm average diameter.

*Color*.—Yellow Green Group 146B, with intonations of Greyed-Red Group 181B occasionally present on surface and stipitate glands.

*Strength*.—Somewhat strong.

*Borne*.—Typically singularly. Multiple flower buds per stem occasionally observed, with 2 to 3 flowers per inflorescence. Flowering laterals typically absent below initiation of inflorescence.

THE PLANT

Growth: Moderately vigorous.

Plant habit: Compact. Upright to bushy. When grown as a 15 cm pot plant, the average plant height is 25 to 30 cm and the average plant width is 15 to 25 cm.

Stems:

*Stem color*.—Young wood: Yellow-Green Group 146B. Older wood: Yellow-Green Group 144A.

*Intonations*.—Greyed-Red Group 181B occasionally present, typically on younger wood.

*Stem surface texture*.—Young wood: Smooth. Older wood: Smooth.

*Length*.—20 to 25 mm average length when grown under commercial greenhouse floral production.

*Diameter*.—2 to 3 mm average diameter.

Prickles: Present.

*Incidence*.—Average of 3 to 7 per each 10 cm of stem.

*Size*.—Average length: 3 to 5 mm.

*Color*.—Immature prickles: Not Observed. Mature prickles: Yellow-Green Group 145C, with intonations of Red Group 51B.

*Shape*.—Linear.

*Anthocyanin*.—Color: Red Group 51B.

Leaves: Normally 5 leaflets on normal leaves in middle of the stem.

*Venation pattern*.—Pyramidal net pattern.

*Leaf size*.—80 to 105 mm (l)×50 to 60 mm (w).

*Abundance*.—Very abundant.

Leaflets:

*Size*.—Average size of the terminal leaflet is 37 mm (l)×20 mm (w).

*Shape*.—Elliptic. Base: Obtuse. Apex: Acute.

*Margins*.—Serrated.

*Surface*.—Upper side: Semi-glossy. Under side: Matte.

*Texture*.—Upper side of leaflet: Smooth. Under side of leaflet: Smooth.

*Color, mature foliage*.—Upper Leaflet Surface: Green Group 139A. Lower Leaflet Surface: Yellow-Green Group 147B.

*Color, juvenile foliage*.—Upper Leaflet Surface: Green Group 137C. Lower Leaflet Surface: Yellow-Green Group 146B.

*Anthocyanin intonation*.—Greyed-Red Group 181B. Location: Margins of juvenile leaflets.

*Arrangement*.—Odd pinnate.

*Venation*.—Reticulate.

Stipules:

*Size*.—10 to 15 mm (l)×3 mm (w).

*Stipule color*.—Yellow-Green Group 144A.

*Anthocyanin*.—Not observed.

*Stipitate glands*.—Abundant on margins only.

*Margins*.—Glandular toothed.

*Texture*.—Smooth and lightly pubescent on upper surface. Glabrous underneath.

*Shape*.—Apex: Apiculate. Base: Winged.

Petiole:

*Length*.—Average 15 to 25 mm.

*Diameter*.—Average 1 mm.

*Petiole color*.—Yellow-Green Group 146A. Underneath: Yellow-Green Group 144A.

*Margins*.—Entire, with limited numbers of small stipitate glands occasionally present.

*Anthocyanin*.—Greyed-Red Group 181B, present on upper surface only.

*Prickles*.—Not present.

*Stipitate glands*.—Limited numbers of stipitate glands occasionally present on margins.

*Texture*.—Smooth and pubescent above, glabrous underneath.

Petiole rachis:

*Length*.—Average 10 to 20 mm.

*Diameter*.—Average 1 mm.

*Color*.—Upper side: Yellow-Green Group 146A. Under side: Yellow-Green Group 146B.

*Anthocyanin*.—Greyed-Red Group 181B, present on upper surface, especially on margins and points of leaflet attachment.

*Margins*.—Limited numbers of stipitate glands occasionally present.

*Prickles*.—A few small prickles occasionally present underneath.

*Stipitate glands*.—Limited numbers of stipitate glands on margins.

*Texture*.—Smooth and pubescent above, glabrous underneath.

Hips/seed formation: None observed.

Winter hardiness: Due to the variety's principal use in greenhouses, winter hardiness has not been evaluated.

Disease resistance: Above average resistance to Powdery mildew (*Sphaerotheca pannosa*) and *Botrytis* (*Botrytis cinerea*) diseases under normal growing conditions in Jackson County, Oreg.

I claim:

1. A new and distinct variety of rose plant, as described and illustrated herein.

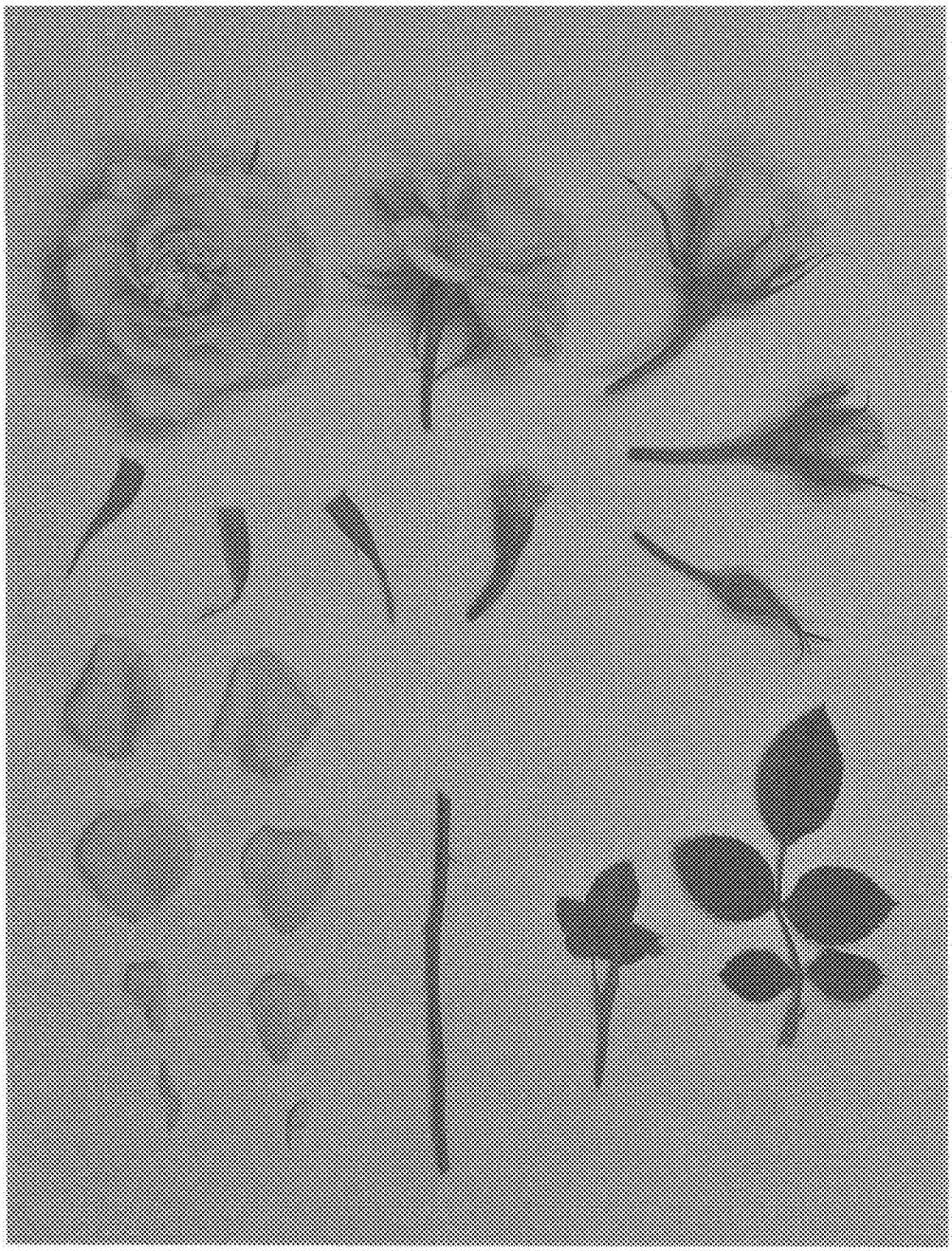

* * * * *